United States Patent
Kraemer et al.

(12)

(10) Patent No.: US 6,455,551 B1
(45) Date of Patent: Sep. 24, 2002

(54) USE OF 1-HYDROXY-2-PYRIDONES FOR TREATING MUCOSA DISEASES WHICH ARE DIFFICULT TO TREAT

(75) Inventors: Karl Theodor Kraemer, Langen; Manfred Schweriner Bohn, Hofheim, both of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/077,685

(22) PCT Filed: Nov. 21, 1996

(86) PCT No.: PCT/EP96/05132

§ 371 (c)(1),
(2), (4) Date: Jun. 3, 1998

(87) PCT Pub. No.: WO97/20560

PCT Pub. Date: Jun. 12, 1997

(30) Foreign Application Priority Data

Oct. 30, 1996 (DE) .......................... 196 43 831

(51) Int. Cl.$^7$ ...................... A61K 31/44; C07D 213/62; C07D 213/643
(52) U.S. Cl. ..................... 514/345; 546/301; 546/302
(58) Field of Search ................. 514/348, 345; 546/301, 302

(56) References Cited

U.S. PATENT DOCUMENTS

| | | | |
|---|---|---|---|
| 3,968,118 A | 7/1976 | Lohaus et al. | 546/283.4 |
| 4,185,106 A | 1/1980 | Dittmar et al. | 514/336 |
| 4,797,409 A | 1/1989 | Lohaus et al. | 514/345 |
| 4,957,730 A | 9/1990 | Bohn et al. | 424/61 |
| 5,066,484 A | 11/1991 | Castrogiovanni et al. | 424/61 |
| 5,120,530 A | 6/1992 | Ferro et al. | 424/61 |
| 5,132,107 A | 7/1992 | Lange | 514/345 |
| 5,264,206 A | 11/1993 | Bohn et al. | 424/61 |
| 5,346,692 A | 9/1994 | Wohlrab et al. | 424/61 |
| 5,494,658 A | 2/1996 | Hänel et al. | 424/70.1 |
| 5,603,939 A | 2/1997 | Ser | 424/401 |
| 5,650,145 A | 7/1997 | Saint-Leger | 424/70.1 |
| 5,675,013 A | 10/1997 | Hani et al. | 514/348 |
| 5,683,681 A | 11/1997 | Ramin et al. | 424/61 |
| 5,753,600 A | 5/1998 | Kamegai et al. | 510/131 |
| 5,866,105 A | 2/1999 | Richter et al. | 424/61 |
| 6,162,420 A | 12/2000 | Bohn et al. | 424/61 |

FOREIGN PATENT DOCUMENTS

| | | |
|---|---|---|
| CA | 2134203 | 4/1995 |
| DE | 38 26 914 A1 | 2/1990 |
| EP | 0 241 918 A2 | 10/1987 |
| EP | 0 313 305 | 4/1989 |
| FR | 2 618 068 | 1/1989 |
| GB | 2 208 149 A | 3/1989 |
| HU | 202098 | 3/1990 |
| WO | 95/17165 | 6/1995 |
| WO | 96/29056 | 9/1996 |

OTHER PUBLICATIONS

H. Hanel et al., "Evaluation of Fungicidal Action in Vitro and in a Skin Model Considering the Influence of Penetration Kinetics of Various Standard Antimycotics," *Annals New York Academy of Sciences*, vol. 544, pp. 329–337, 1988.

P.C. Braga et al., "Inhibition of Candida albicans Adhesiveness to Human Buccal and Vaginal Cells by Sub–inhibitory Concentrations of Rilopirox," *Arzneim.–Forsch./Drug Res.*, vol. 45, No. 1, pp. 84–87, 1995.

W. Raether et al., "Rilopirox—a New Hydroxypyridone Antifungal with Fungicidal Properties," *Mycoses*, Bd. 33, No. 4, pp. 191–202, Apr. 5, 1990.

Yoshimasa et al., "The sebum lipid assimilation and the growth inhibition of Pityrosporum ovale ($1^{st}$ report)," *J. SCCJ*, vol. 22(3), pp. 165–170 (1988).

Saint–Leger et al., "The role of the resident microflora in the pathogenesis of dandruff," *J. SOC. COSMET. CHEM.*, vol. 40, pp. 109–117 (1989).

Martindale, The Extra Pharmacopoeia $30^{th}$ Ed., London The Pharmaceutical Press 1993, pp. 332, 1609.

Montana, et al., "A Double–Blind, Vehicle–Controlled Study of the Safety and Efficacy of Fungoid Tincture® in Patients with Distal Subungual Onychmycosis of the Toes," *Cutis*, 53:313–316 (1994).

*Primary Examiner*—Charanjit S. Aulakh
(74) *Attorney, Agent, or Firm*—Finnegan, Henderson, Farabow, Garrett & Dunner LLP

(57) ABSTRACT

The compound of the formula I

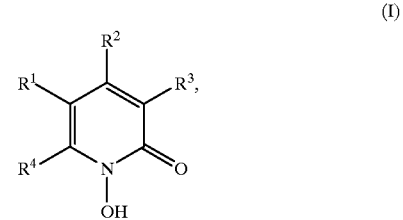

(I)

is suitable for the preparation of pharmaceuticals for the treatment of fungal disorders caused by azole-resistant fungi.

13 Claims, No Drawings

USE OF 1-HYDROXY-2-PYRIDONES FOR TREATING MUCOSA DISEASES WHICH ARE DIFFICULT TO TREAT

The number of mucosal disorders which are difficult to treat has considerably increased in recent times, and the increasing trend continues. The mucosal disorders which are difficult to treat nowadays include primarily candidoses of the oral and vaginal mucosa.

Candidoses are defined as infections usually caused by *Candida albicans*, but also by a large number of other Candida species which grow opportunistically (*C. krusei, C. tropicalis, Candida glabrata* and many others). The yeast-like fungi which are often present anyway in the oral cavity, the gastrointestinal tract and the vagina grow under particular conditions and assume parasitic/pathogenic characteristics. Yeast-like fungi are able in some circumstances to colonize the skin and its appendages, all mucosae near the skin and several internal organs (esophagus, lung etc.) and, in this event, induce a remarkably wide range of disorders.

The occurrence of a candidosis may be favored in particular by pregnancy, metabolic disorders, infectious diseases, tumors and immunodeficiencies. Locally favoring factors are regarded as being mechanical irritation (for example dentures), occlusion, moisture and moist heat.

The occurrence of extensive oral candidosis is nowadays regarded in most countries as one of the principal clinical signs of impaired functioning of the immune system. Persistent oral candidoses indicate in many HIV patients the transition to immunodecompensation. In advanced immunodeficiency there are also erosive, and sometimes ulcerative, inflammations involving the gingiva, and candidal balanitis, candidal vulvitis and Candida-related anal eczema are not uncommon. Intestinal infections and candidal sepsis are likewise observed.

In immunocompetent patients, nystatin is regarded as the agent of choice for local treatment of Candida infections, but clinical experience shows that nystatin therapy on its own is often insufficient in HIV-infected immunodeficient patients. In these cases, systemic therapy with antimycotics of the azole type is widely used. Candida strains resistant to azoles were virtually unknown up to 1989. However, the treatment of vaginal candidoses has often proven difficult due to the occurrence of mixed infections with the protozoal strains *Trinchomonas vaginalis* and *Entamoeba histolytica*.

However, since the use of fluconazole for preventing recurrence of oropharyngeal candidoses in HIV patients, the number of azole resistances which have become known has increased dramatically. Up to and including the 1st half of 1995, 98 publications in the specialist literature reported resistance of Candida strains to azoles.

The documents EP 0 241 918 or U.S. Pat. No. 4,797,409 describe the preparation of 1-hydroxy-2-pyridones and their use for controlling mainly infections by fungi and yeast, and pharmaceuticals containing these compounds.

It is therefore an object of the present invention to provide topical pharmaceutical formulations which are suitable for breaking through exsistent intrinsic and acquired resistances of Candida strains to azoles, while simultaneously having activity on the problem organisms *Trinchomonas vaginalis* and *Entamoeba histolytica*.

It has now been found that compounds of the formula I are outstandingly suitable for the treatment of candidoses caused by yeast strains with intrinsic and acquired azole resistance. Said compounds are also distinguished by their activity, which is sufficient for therapeutic purposes, on the problem organisms *Trinchomonas vaginalis* and *Entamoeba histolytica* which are often the cause of the development of mixed infections in cases of vaginal candidosis.

The invention relates to the use of the compound of the formula I

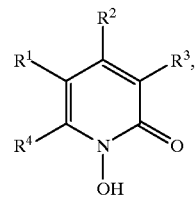

(I)

in which $R^1$, $R^2$ and $R^3$, which are identical or different, are hydrogen atom or alkyl with 1–4 carbon atoms, and $R^4$ is a saturated hydrocarbon radical with 6 to 9 carbon atoms or a radical of the formula II

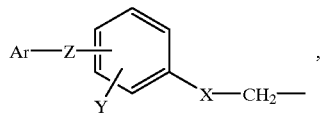

(II)

where
 X is S or O,
 Y is a hydrogen atom or up to 2 halogen atoms such as chlorine and/or bromine,
 Z is a single bond or the divalent radicals O, S, —CR$_2$— (R=H or $C_1$–$C_4$-alkyl) or other divalent radicals with 2–10 carbon and, where appropriate, oxygen and/or sulfur atoms linked to form a chain, and—when the radicals contain 2 or more oxygen and/or sulfur atoms—the latter must be separated from one another by at least 2 carbon atoms, and where 2 adjacent carbon atoms can also be linked together by a double bond, and the free valencies of the carbon atoms are saturated by H and/or $C_1$–$C_4$ alkyl groups,
 Ar is an aromatic ring system which has up to two rings and can be substituted by up to three radicals from the group of fluorine, chlorine, bromine, methoxy, $C_1$–$C_4$-alkyl, trifluoromethyl and trifluoromethoxy,
for the preparation of a pharmaceutical for the treatment of fungal disorders caused by azole-resistant fungi.

The compounds according to the invention are furthermore suitable for the treatment of trichomoniasis, one of the commonest causes, which is spread around the world, of non-gonorrheal urethritis. The disorder is caused by the pathogen *Trinchomonas vaginalis* which is one of the protozoa.

The carbon chain members in the "Z" radicals are preferably CH$_2$ groups. If the CH$_2$ groups are substituted by $C_1$–$C_4$-alkyl groups, CH$_3$ and $C_2H_5$ are preferred substituents.

Examples of "Z" radicals are:

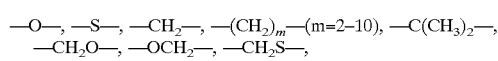

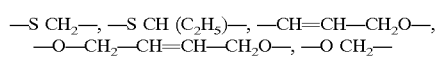

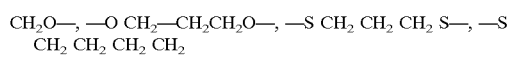

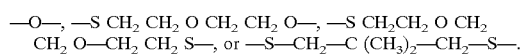

The radical "S" is a sulfur atom, and the radical "O" is an oxygen atom. The term "Ar" means phenyl and condensed systems such as naphthyl, tetrahydronaphthyl and indenyl, and isolated systems such as those derived from biphenyl, diphenylalkanes, diphenyl ethers and diphenyl thioethers.

Principal representatives of the class of compounds characterized by the formula I are:

6-[4-(4-chlorophenoxy)phenoxymethyl]-1-hydroxy4-methyl-2-pyridone;

6-[4-(2,4-dichlorophenoxy)phenoxymethyl]-1-hydroxy-4-methyl-2-pyridone;

6-(4-biphenylyloxymethyl)-1-hydroxy-4-methyl-2-pyridone;

6-(4-benzylphenoxymethyl)-1-hydroxy-4-methyl-2-pyridone;

6-[4-(2,4-dichlorobenzyloxy)phenoxymethyl]-1-hydroxy-4-methyl-2-pyridone;

6-[4-(4-chlorophenoxy)phenoxymethyl]-1-hydroxy-3,4-dimethyl-2-pyridone;

6-[4-(2,4-dichlorobenzyl)phenoxymethyl]-1-hydroxy-3,4-dimethyl-2-pyridone;

6-[4-(cinnamyloxy)phenoxymethyl]-1-hydroxy4-methyl-2-pyridone;

1-hydroxy-4-methyl-6-[4-(4-trifluoromethylphenoxy)phenoxymethyl]-2-pyridone;

1-hydroxy4-methyl-6-cyclohexyl-2-pyridone or 1-hydroxy4-methyl-6-(2,4,4-trimethylpentyl)-2-pyridone.

The abovementioned compounds of the formula I can be employed both in free form and in the form of salts, and use in free form is preferred. The compounds of the formula I to be employed in the formulations can be prepared, for example, by processes disclosed in U.S. Pat. Nos. 2,540,218 or 4,797,409.

The term "azole-resistant fungi" means all species of fungi or yeasts which have become resistant to antimycotics, for example to antimycotics which contain azole residues, such as fluconazole.

Immunosuppressed patients are preferably treated such as diabetics, asthmatics, smokers, AIDS patients, patients before and after transplants, cancer patients, patients chronically treated with antibiotics, cytostatics or corticosteroids, patients with antimycotic-resistant fungi, in particular patients with fluconazole-resistant fungi or elderly people.

Suitable for the use of said compounds according to the invention are liquid, semisolid and solid pharmaceutical formulations, in particular solutions, cream, ointment and gel formulations, and pastilles and pessaries.

The active substance is incorporated into the formulations according to the invention in amounts which are normally between about 0.05 and about 5%, preferably between 0.1 and 1%.

Topical treatment of candidoses caused by yeast strains with intrinsic and acquired azole resistance with the pharmaceuticals according to the invention is able to achieve an effective cure.

The compositions according to the invention can also be employed successfully for the treatment of vaginal candidoses with mixed infections by the protozoal strains *Trinchomonas vaginalis* and *Entamoeba histolytica*.

EXAMPLE 1

A formulation according to the invention has the following composition:

| | |
|---|---|
| 6-[4-(4-Chlorophenoxy)phenoxymethyl]-1-hydroxy-4-methyl-2(1H)-pyridone | 0.50% |
| Hydroxyethylcellulose | 1.50% |
| Polyethylene glycol 7 glyceryl cocoate | 5.00% |
| 1,2-Propylene glycol | 10.00% |
| Isopropyl alcohol | 20.00% |
| Demineralized water | 63.00% |

EXAMPLE 2

A formulation according to the invention has the following composition:

| | |
|---|---|
| 6-[4-(4-Chlorophenoxy)phenoxymethyl]-1-hydroxy-4-methyl-2(1H)-pyridone | 1.00% |
| 2-Octyldodecanol | 5.00% |
| Liquid paraffin | 5.00% |
| Cetyl alcohol | 5.00% |
| Stearyl alcohol | 5.00% |
| Myristyl alcohol | 5.00% |
| Polyoxyethylene 20 sorbitan monostearate | 3.00% |
| Sorbitan monostearate | 2.00% |
| Demineralized water | 69.00% |

EXAMPLE 3

A formulation according to the invention has the following composition:

| | |
|---|---|
| 6-Cyclohexyl-1-hydroxy-4-methyl-2(1H)-pyridone | 5 mg |
| Polyethylene glycol 1500 | 1500 mg |
| Polyethylene glycol 4000 | 1000 mg |
| Polyethylene glycol 6000 | 165 mg |
| Sodium bicarbonate | 180 mg |
| Tartaric acid | 150 mg |

EXAMPLE 4

A formulation according to the invention has the following composition:

| | |
|---|---|
| 6-[4-(4-Chlorophenoxy)phenoxymethyl]-1-hydroxy-4-methyl-2(1H)-pyridone | 10 mg |
| Tylose C 1000 P | 30 mg |
| Polyethylene glycol 6000 | 500 mg |
| Mannitol | 305 mg |
| Sodium stearyl fumarate | 5 mg |

EXAMPLE 5

Test of Efficacy

Determination of the efficacy of 6-[4-(4-chlorophenoxy)phenoxymethyl]-1-hydroxy4-methyl-2(1H)-pyridone (Compound 1) on fluconazole-resistant strains of *Candida albicans*

Fluconazole-resistant strains of *Candida albicans* are isolated from patients who have been treated, for example, with fluconazole for more than one year. For this purpose, samples are taken from the patients' mouths and applied, undiluted or diluted 1:100, to an RPMI 1640 agar (Gibco/BRL, Life Technologies GmbH, D-76339 Eggenstein) which contains about 1.0 μg/ml fluconazole. Resistant *Candida albicans* strains are isolated, further purified on agar and stored isolated in peptone/dextrose slant agar tubes.

The activity of Compound 1 and fluconazole is determined by the microtiter dilution technique in RPMI 1640 medium. The growth medium RPMI 1640 buffered with 0.165 M morpholinopropanesulfonic acid pH 7.0 is introduced into 96-well microtiter plates. Serial dilutions by a factor of 2 are prepared for Compound 1 and fluconazole to result in final concentrations of 256 to 0.002 μg/ml of Compound 1 and fluconazole. The microtiter plates prepared in this way are incubated with the Candida strains to be tested. For comparison purposes, the two *Candida albicans* strains ATCC 90028 and 90029 which are not resistant to fluconazole are included in the test. The initial cell count is 1–5 ×10$^3$ colony-forming units per ml of growth medium. The microtiter plates are incubated at 35° C. for 48 hours. The minimum inhibitory concentration is determined by photometry at 510 nm. Table 1 shows the results:

TABLE 1

| Strain | Minimum inhibitory concentration (MIC) (μg/ml) | |
| --- | --- | --- |
| | Fluconazole | Compound 1 |
| Candida albicans ATCC 90028 | 0.5 | 1 |
| Candida albicans ATCC 90029 | 1 | 0.5 |
| Candida albicans 94/3 | 32 | 2 |
| Candida albicans 94/14 | 32 | 2 |
| Candida albicans 94/57 | >256 | 1 |
| Candida albicans 94/62 | >256 | 1 |
| Candida albicans 94/90 | >256 | 1 |
| Candida albicans 94/118 | >256 | 2 |
| Candida albicans 94/134 | >256 | 1 |
| Candida albicans 94/138 | >256 | 1 |
| Candida albicans 94/222 | >256 | 1 |
| Candida albicans 94/231 | >256 | 1 |
| Candida albicans B6 | 1 | 1 |
| Candida albicans B70 | >256 | 1 |
| Candida albicans B75 | 2 | 1 |
| Candida krusei B1 | 32 | 0.5 |
| Candida krusei B4 | 16 | 1 |
| Candida glabrata B12 | 4 | 0.5 |
| Candida glabrata B14 | 2 | 0.5 |
| Candida glabrata B18 | 8 | 0.5 |
| Candida glabrata B21 | 8 | 1 |
| Candida glabrata B35 | 8 | 1 |
| Candida glabrata B37 | 16 | 1 |
| Candida glabrata B38 | 16 | 1 |
| Candida glabrata B39 | 8 | 0.5 |
| Candida glabrata B40 | 16 | 1 |
| Candida glabrata B50 | 16 | 0.5 |
| Candida glabrata B51 | 32 | 0.5 |
| Candida guillermondii B47 | 4 | 1 |

Table 1 shows that Compound 1 impedes the growth of Candida strains in a very narrow concentration range—irrespective of existent fluconazole resistance.

EXAMPLE 6

In vitro activity of the Compound 1 on protozoa

| | n = | MIC (μg/ml) |
| --- | --- | --- |
| Trichomonas vaginalis | 5 | 31.2$_{(3)}$, 125$_{(2)}$ |
| Entamoeba histolytica | 4 | 31.2, 62.5$_{(3)}$ | n = number of strains investigated;
the number given in parentheses corresponds to the number of tested strains with which the stated MIC was determined.

What is claimed is:
1. A method for treating a fungal disorder caused by at least one fluconazole-resistant fungus or at least one fluconazole-resistant yeast, or a combination thereof, in a human or animal patient in need of such treatment, comprising topically applying to the patient at least one compound of formula I, at least one pharmaceutically acceptable salt thereof, or a combination of the foregoing:

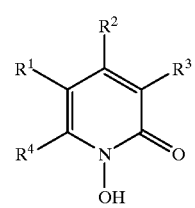

(I)

where $R^1$, $R^2$, and $R^3$, which are identical or different, are H or alkyl having 1 to 4 carbon atoms, and $R^4$ is a saturated hydrocarbon radical having 6 to 9 carbon atoms or a radical of formula II:

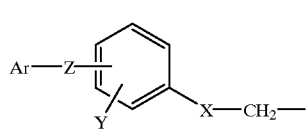

(II)

where:
  X is S or O;
  Y is H, or 1 or 2 identical halogen atoms, or a mixture of 2 different halogen atoms;
  Z is a single bond, or
  a bivalent radical comprising
    (1) O, or
    (2) S, or
    (3) —CR$_2$—, where R is H or (C$_1$–C$_4$)-alkyl, or
    (4) from 2 to 10 carbon atoms linked in the form of a chain, which optionally further comprises one or more of the following:
      (i) a carbon-carbon double bond, or
      (ii) O, S, or a mixture thereof, wherein if 2 or more O or S atoms or a mixture thereof are present, each O or S atom is separated by at least 2 carbon atoms; and,
  in any of the foregoing bivalent radicals, free valences of the carbon atoms of said bivalent radical are saturated by H, (C$_1$–C$_4$)-alkyl, or a mixture thereof; and
  Ar is an aromatic ring system having one or two rings which can be substituted by one, two, or three radicals, which may be identical or different, which are halogen, methoxy, $(C_1-C_4)$-alkyl, trifluoromethyl, or trifluoromethoxy.

2. A method for treating a fungal disorder caused by at least one fluconazole-resistant fungus or at least one fluconazole-resistant yeast, or a combination thereof, in a human or animal patient in need of such treatment, as claimed in claim 1, in which Ar is phenyl, $R^1$ and $R^3$ are hydrogen, and $R^2$ is methyl.

3. A method for treating a fungal disorder caused by at least one fluconazole-resistant fungus or at least one fluconazole-resistant yeast, or a combination thereof, in a human or animal patient in need of such treatment, as claimed in claim 1, in which Ar is derived from biphenyl, diphenylalkane, or diphenyl ether.

4. A method for treating a fungal disorder caused by at least one fluconazole-resistant fungus or at least one fluconazole-resistant yeast, or a combination thereof, in a human or animal patient in need of such treatment, as claimed in claim 1, in which Z is a single bond or O.

5. A method for treating a fungal disorder caused by at least one fluconazole-resistant fungus or at least one fluconazole-resistant yeast, or a combination thereof, in a human or animal patient in need of such treatment, as claimed in claim 1 in which the at least one compound of formula I comprises 6-[4-(4-chlorophenoxy)-phenoxymethyl]-1-hydroxy-4-methyl-2-pyridone, 1-hydroxy-4-methyl-6-cyclohexyl-2-pyridone, 1-hydroxy-4-methyl-6-(2,4,4-trimethylpentyl)-2-pyridone, at least one pharmaceutically acceptable salt thereof, or a combination of the foregoing.

6. A method for treating a fungal disorder caused by at least one fluconazole-resistant yeast in a human or animal patient in need of such treatment, as claimed in claim 1 in which the fluconazole-resistant yeast has an intrinsic fluconazole resistance.

7. A method for treating a fungal disorder caused by at least one fluconazole-resistant yeast in a human or animal patient in need of such treatment, as claimed in claim 1 in which the fluconazole-resistant yeast has an acquired fluconazole resistance.

8. A method for treating a fungal disorder caused by at least one fluconazole-resistant fungus or at least one fluconazole-resistant yeast, or a combination thereof, in a human or animal patient in need of such treatment, as claimed in claim 1 in which the disorder is vaginal candidoses.

9. A method for treating a fungal disorder caused by at least one fluconazole-resistant fungus or at least one fluconazole-resistant yeast, or a combination thereof, in a human or animal patient in need of such treatment, as claimed in claim 1 wherein the compound of formula I destroys or inhibits the growth of protozoa from groups Trichomonas or Entamoeba, or a combination thereof.

10. A method for treating a fungal disorder caused by at least one fluconazole-resistant fungus or at least one fluconazole-resistant yeast, or a combination thereof, in a human or animal patient in need of such treatment, as claimed in claim 1 wherein the compound of formula I destroys or inhibits the growth of *Trichomonas vaginitis, Entamoeba hystolytica*, or a combination thereof.

11. A method for treating a fungal disorder caused by at least one fluconazole-resistant fungus or at least one fluconazole-resistant yeast, or a combination thereof, in a human or animal patient in need of such treatment, as claimed in claim 1, in which the fungal disorder affects oral mucosa of the patient.

12. A method for treating a fungal disorder caused by at least one fluconazole-resistant fungus or at least one fluconazole-resistant yeast, or a combination thereof, in a human or animal patient in need of such treatment, as claimed in claim 1, in which the fungal disorder affects vaginal mucosa of the patient.

13. A pharmaceutical composition useful for topically treating a fungal disorder caused by at least one fluconazole-resistant fungus or at least one fluconazole-resistant yeast, or a combination thereof, in a human or animal patient in need of such treatment, comprising at least one pharmaceutically acceptable carrier and an efficacious amount of at least one compound of formula I, at least one pharmaceutically acceptable salt thereof, or a combination of the foregoing:

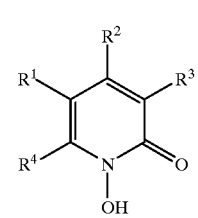

(I)

where $R^1$, $R^2$, and $R^3$, which are identical or different, are H or alkyl having 1 to 4 carbon atoms, and $R^4$ is a saturated hydrocarbon radical having 6 to 9 carbon atoms or a radical of formula II:

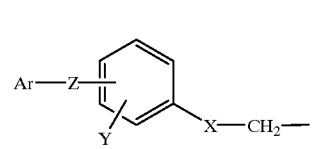

(II)

where:
X is S or O;
Y is H, or 1 or 2 identical halogen atoms, or a mixture of 2 different halogen atoms;
Z is a single bond, or
a bivalent radical comprising
  (1) O, or
  (2) S, or
  (3) —$CR_2$—, where R is H or $(C_1-C_4)$-alkyl, or
  (4) from 2 to 10 carbon atoms linked in the form of a chain, which optionally further comprises one or more of the following:
    (i) a carbon-carbon double bond, or
    (ii) O, S, or a mixture thereof, wherein if 2 or more O or S atoms or a mixture thereof are present, each O or S atom is separated by at least 2 carbon atoms; and,
in any of the foregoing bivalent radicals, free valences of the carbon atoms of said bivalent radical are saturated by H, $(C_1-C_4)$-alkyl, or a mixture thereof; and Ar is an aromatic ring system having one or two rings which can be substituted by one, two, or three radicals, which may be identical or different, which are halogen, methoxy, $(C_1-C_4)$-alkyl, trifluoromethyl, or trifluoromethoxy.

* * * * *

UNITED STATES PATENT AND TRADEMARK OFFICE
CERTIFICATE OF CORRECTION

PATENT NO.   : 6,455,551 B1
DATED        : September 24, 2002
INVENTOR(S)  : Karl T. Kraemer et al.

It is certified that error appears in the above-identified patent and that said Letters Patent is hereby corrected as shown below:

Column 7,
Line 28, after "1-hydroxy-4-methyl-6" delete the space.
Line 29, after "4-methyl-6(2,4,4-trimethylpentyl" delete the space.

Signed and Sealed this

Fourth Day of February, 2003

JAMES E. ROGAN
*Director of the United States Patent and Trademark Office*